(12) United States Patent
Duarte et al.

(10) Patent No.: US 6,685,656 B1
(45) Date of Patent: Feb. 3, 2004

(54) ULTRASONIC TREATMENT FOR WOUNDS

(75) Inventors: Luiz R. Duarte, San Paulo (BR); Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 470 days.

(21) Appl. No.: 09/229,855

(22) Filed: Jan. 13, 1999

Related U.S. Application Data (62) Division of application No. 08/886,217, filed on Jul. 1, 1997, now Pat. No. 5,904,659, which is a continuation of application No. 08/799,240, filed on Feb. 14, 1997, now abandoned.

(51) Int. Cl.[7] .............................................. A61N 7/00
(52) U.S. Cl. .......................................................... 601/2
(58) Field of Search .................... 601/2–4, 46; 600/437, 600/447, 459; 310/311, 322, 348, 367

(56) References Cited

U.S. PATENT DOCUMENTS

| | | | |
|---|---|---|---|
| 3,499,437 A | | 3/1970 | Balamuth |
| 3,760,799 A | * | 9/1973 | Crowson ........................ 601/2 |
| 4,105,017 A | | 8/1978 | Ryaby et al. |
| 4,127,125 A | | 11/1978 | Takemoto et al. |
| 4,315,503 A | | 2/1982 | Ryaby et al. |
| 4,361,154 A | | 11/1982 | Pratt, Jr. |
| 4,421,119 A | | 12/1983 | Pratt, Jr. |
| 4,530,360 A | | 7/1985 | Duarte |
| 4,556,066 A | | 12/1985 | Semrow |
| 4,708,127 A | | 11/1987 | Abdelghani |
| 4,763,661 A | | 8/1988 | Sommer et al. |
| 4,774,959 A | | 10/1988 | Palmer et al. |
| RE32,782 E | | 11/1988 | Pratt, Jr. |
| 4,787,070 A | | 11/1988 | Suzuki et al. |
| 4,787,888 A | * | 11/1988 | Fox ................................. 601/2 |

(List continued on next page.)

FOREIGN PATENT DOCUMENTS

| | | |
|---|---|---|
| CA | 1328485 | 4/1994 |
| JP | SHO 62-47359 | 3/1987 |
| JP | HEI 4-82568 | 3/1992 |
| JP | HEI 4-82569 | 3/1992 |
| JP | HEI 5-269159 | 10/1993 |
| WO | WO 88/00845 | 2/1988 |
| WO | WO 95/33416 | 12/1995 |

OTHER PUBLICATIONS

Abstract, (Proceedings of the IV Brazilain Congress on Biomedical Engineering) "Ultrasound in the Treatment of Fractures", 1977.

(List continued on next page.)

Primary Examiner—Ruth S. Smith
(74) Attorney, Agent, or Firm—Bruce D. Gray (57) ABSTRACT

A portable therapeutic device and method of use generate longitudinally propagating ultrasound and shear waves generated by such longitudinally propagating ultrasound to provide effective healing of wounds. A transducer having an operative surface is disposed substantially adjacent to the wound to emit ultrasound to propagate in the direction of the wound to promote healing. Reflections of the ultrasound by bone tissue, by skin layers, or by internally disposed reflective media propagate toward the wound as longitudinal waves, with shear waves generated by the longitudinal waves for the healing of the wound. A focusing element is used for focusing the propagation of the ultrasound at a predetermined angle toward the wound. The operative surface of the transducer may be annularly shaped to encircle the wound to convey the ultrasound and/or reflected ultrasound thereto. A housing may be provided for positioning the transducer near a portion of the skin near the wound, and for indenting the skin to form a cavity, with the transducer disposed in the cavity to emit the ultrasound toward an internal surface of the wound. Fixture structures, such as adjustable straps, may extend about a portion of the body to position the transducer near the wound.

11 Claims, 8 Drawing Sheets

U.S. PATENT DOCUMENTS

| | | | |
|---|---|---|---|
| 4,830,015 A | 5/1989 | Okazaki | |
| 4,855,911 A | 8/1989 | Lele et al. | |
| 4,867,169 A | 9/1989 | Machida et al. | |
| 4,905,671 A | 3/1990 | Senge et al. | |
| 4,913,157 A | 4/1990 | Pratt, Jr. et al. | |
| 4,926,870 A | 5/1990 | Brandenburger | |
| 4,932,951 A | 6/1990 | Liboff et al. | |
| 4,936,303 A | 6/1990 | Detwiler et al. | |
| 4,941,474 A | 7/1990 | Pratt, Jr. | |
| 4,979,501 A | 12/1990 | Valchanov et al. | |
| 4,986,275 A | 1/1991 | Ishida et al. | |
| 4,993,413 A | 2/1991 | McLeod et al. | |
| 5,003,965 A | 4/1991 | Talish et al. | |
| 5,054,490 A | 10/1991 | Rossman et al. | |
| 5,067,940 A | 11/1991 | Liboff et al. | |
| 5,088,976 A | 2/1992 | Liboff et al. | |
| 5,100,373 A | 3/1992 | Liboff et al. | |
| 5,103,806 A | 4/1992 | McLeod et al. | |
| 5,106,361 A | 4/1992 | Liboff et al. | |
| 5,134,999 A | 8/1992 | Osipov | |
| 5,140,988 A | 8/1992 | Stouffer et al. | |
| 5,143,073 A | 9/1992 | Dory | |
| 5,172,692 A | 12/1992 | Kulow et al. | |
| 5,178,134 A | 1/1993 | Vago | |
| 5,186,162 A | 2/1993 | Talish et al. | |
| 5,191,880 A | 3/1993 | McLeod et al. | |
| 5,209,221 A | 5/1993 | Riedlinger | |
| 5,211,160 A | 5/1993 | Talish et al. | |
| 5,235,981 A | 8/1993 | Hascoet et al. | |
| 5,259,384 A | 11/1993 | Kaufman et al. | |
| 5,273,028 A | 12/1993 | McLeod et al. | |
| 5,284,143 A | 2/1994 | Rattner | |
| 5,285,788 A | 2/1994 | Arenson et al. | |
| 5,309,898 A | 5/1994 | Kaufman et al. | |
| 5,314,401 A | 5/1994 | Tepper | |
| 5,316,000 A | 5/1994 | Chapelon et al. | |
| 5,318,561 A | 6/1994 | McLeod et al. | |
| 5,327,890 A | 7/1994 | Matura et al. | |
| 5,351,389 A | 10/1994 | Erickson et al. | |
| 5,376,065 A | 12/1994 | McLeod et al. | |
| 5,413,550 A * | 5/1995 | Castel | 601/2 |
| 5,415,167 A | 5/1995 | Wilk | |
| 5,417,215 A | 5/1995 | Evans et al. | |
| 5,448,994 A | 9/1995 | Iinuma | |
| 5,496,256 A | 3/1996 | Bock et al. | |
| 5,520,612 A | 5/1996 | Winder et al. | |
| 5,547,459 A | 8/1996 | Kaufman et al. | |
| 5,556,372 A | 9/1996 | Talish et al. | |
| 5,578,060 A | 11/1996 | Pohl et al. | |
| 5,630,837 A * | 5/1997 | Crowley | 601/2 |
| 5,690,608 A * | 11/1997 | Watanabe et al. | 601/2 |
| 5,904,659 A | 5/1999 | Duarte et al. | |

OTHER PUBLICATIONS

Abstract, (Proceedings of the 11th Int'l. Conference on Medical and Biological Engineering) "Ultrasonic Stimulation of Fracture Healing", 1976.

Abstract, (Proceedings of the III Congress on Biomedical Engineering) "Ultrasonic Action on Callus Formation in Bones", 1975.

Arai et al., "The Effect of Ultrasound Stimulation on Disuse Osteoporosis", BRAGS 17, 1993.

L.R. Duarte, "The Stimulation of Bone Growth by Ultrasound", Arch Orthop Traum Surg (1983) 101:153–159.

Maurice Hilário, "Low–Intensity Ultrasound Radiation in the Tissue Repair of Trophic Leg Ulcers", 1983, University of Sao Paulo, pp. 1–125.

* cited by examiner

ULTRASONIC TREATMENT FOR WOUNDS

PRIORITY

The present application is a divisional application of U.S. patent application Ser. No. 08/886,217 filed on Jul. 1, 1997, now U.S. Pat. No. 5,904,659 issued on May 18, 1999, which is a continuation application of U.S. patent application Ser. No. 08/799,240 filed on Feb. 14, 1997 now abandoned.

BACKGROUND OF THE INVENTION

1. Field of the Invention

This disclosure relates to the non-invasive application of ultrasonic energy to enhance and/or accelerate the process of wound healing, and more particular, to the healing of wounds including ulcers, such as venous ulcers.

2. Description of the Related Art

Venous ulcers on human legs have proven difficult to treat, for example, because of the lack of vascularization in and around the wound.

The term "wound" for the purposes of "wound healing", as used throughout the present disclosure, includes ulcers such as venous ulcers as well as burns, ulcerated wounds due to, for example, diabetes, surgical incisions or other surgical cuttings including stitched surgical cuttings, skin grafts, hair transplants, re-vascularization, bed sores, tissue dehiscence, and ligament and tendon repair and reconstruction. In general, as used throughout the present disclosure, the term "wound healing" encompasses addressing damage to, repair of, or restoration of soft tissue.

U.S. Pat. No. 4,530,360 to Duarte (hereafter "Duarte"), describes a basic therapeutic technique and apparatus for applying ultrasonic pulses from an ultrasonic applicator placed on the skin at a location adjacent a bone injury. Duarte gives a range of radio frequency (RF) signals for creating the ultrasound, ultrasonic power density levels, a range of duration of each ultrasonic pulse, and a range of ultrasonic pulse frequencies. The length of daily treatment is also described in Dart. The Dart patent is incorporated herein by reference.

U.S. Pat. Nos. 5,003,965 and 5,186,162, both to Tallish and Lifshey (hereafter "Tallish '965" and "Tallish '162", respectively) describe an ultrasonic delivery system in which the RF generator and transducer are both part of a modular applicator unit which is placed at the skin location. The signals controlling the duration of ultrasonic pulses and the pulse repetition frequency are generated apart from the applicator unit. Tallish '965 and Tallish '162 also describe fixture apparatus for attaching the applicator unit so that the operative surface is adjacent to the skin location. In one application described in Tallish '965 and Tallish '162, the skin is surrounded by a cast.

U.S. Pat. No. 5,211,160 to Tallish and Lifshey (hereafter "Tallish '160") also describes a fixture apparatus which is mounted on uncovered body parts; i.e. without a cast or other medical wrapping. Tallish '160 also describes various improvements to the applicator unit. Each of Tallish '965, Tallish '162, and Tallish '160 is incorporated herein by reference.

U.S. Pat. No. 5,755,746 to Lifshey and Talish (hereafter "Lifshey '746"); U.S. Pat. No. 5,626,554 to Ryaby, Talish and McCabe (hereafter "Ryaby '554"); U.S. Pat. No. 5,556,372 to Talish, Ryaby, Scowen and Urgovitch (hereafter "Talish '372"); and U.S. Pat. No. 5,520,612 to Winder, Talish and Ryaby (hereafter "Winder '612"), entitled Locator Method and Apparatus, Gel Containment Structure, Apparatus for Ultrasonic Bone Treatment, and Acoustic System for Bone-fracture Therapy, respectively, provides ultrasonic apparatus and methods which are applicable to wound healing. Lifshey '746, Ryaby '554, Talish '372, and Winder '612 are incorporated herein by reference.

In general, an ultrasound carrier frequency between 20 kHz and 10 MHZ coupled with a relatively low-frequency modulating signal, such as 5 Hz to 10 kHz, and a spatial peak temporal average acoustic intensity, such as an intensity less than about 100 milliwatts/cm$^2$, should aid in and should be effective in wound healing.

Heretofore, such techniques have not been applied to heal wounds by internal application of ultrasound, such as using reflection of ultrasonic waves by reflection from internal tissue such as bone.

SUMMARY

It is herein recognized that both longitudinally propagating ultrasound and shear waves generated by a transducer mechanism and/or by such longitudinally propagating ultrasound provide effective healing of wounds.

A portable therapeutic device and method of use thereof for healing a wound includes a transducer having an operative surface, with the transducer, disposed substantially adjacent to the wound to emit ultrasound to propagate in the direction of the wound for the healing thereof. Reflections of the ultrasound by bone tissue and by skin layers propagate toward the wound as longitudinal waves for the healing thereof, and shear waves are generated by the longitudinal waves and/or the reflected longitudinal waves for the healing of the wound.

The transducer may include an axis and a focusing element for focusing the propagation of the ultrasound at a predetermined angle with respect to the axis, with the focused ultrasound propagating toward the wound for the healing thereof.

Alternative configurations of the operative surface of the transducer include an annularly shaped operative surface for emitting the ultrasound therefrom, with the wound encircled by the operative surface for receiving the ultrasound and/or reflected ultrasound.

A housing may be provided for positioning the transducer substantially adjacent to a portion of the skin substantially adjacent to the wound, and for causing the portion of the skin to form a cavity, with the operative surface of the transducer disposed in the cavity to emit the ultrasound to an internal surface of the wound for the healing thereof.

Reflective media may be internally disposed within the body having the wound for reflecting the ultrasound from the transducer to propagate toward the wound for the healing thereof. Fixture structures, extending about a portion of the body having the wound, may also be provided for positioning the transducer substantially adjacent to the skin substantially adjacent to the wound. The fixture structure may include an adjustable strap.

In other embodiments, the transducer may be a rod-shaped operative surface having an axis for emitting the ultrasound radially toward the wound for the healing thereof.

Using the disclosed therapeutic devices, wounds are safely and simply treated, with such wounds as venous ulcers responsive to therapeutic ultrasound to be healed effectively. Such therapeutic devices and methods of use provide for wound treatment by modest adaption of existing devices for delivering ultrasound in therapeutic settings.

In one embodiment, a device is provided for delivering an ultra-high-frequency carrier signal for low power excitation of an acoustic transducer which is acoustically coupled to a limb or other part of a living body. The transducer is positioned adjacent an external skin location in the vicinity of the external border of the wound on the skin to provide a surgical, non-invasive transcutaneous delivery of at least part of its acoustic energy directed from the external skin location toward a portion of a bone located within the body in the vicinity of the boundary of the wound internal to the body. The boundary of the wound internal to the body is also referred to herein as the internal or interior surface of the wound.

Once the acoustic energy enters the body, it passes into internal body tissue and/or fluids. The acoustic energy, in the form of ultrasonic pulses, is reflected off the surface of underlying bone or other ultrasound reflective material, and the reflected ultrasound travels toward at least part of the internal surface or underside of the wound. Healing of the wound at the internal surface by the generation of epithelial cells is enhanced via the acoustic stimulation.

Preferably, a low frequency signal which is present as a modulation of the carrier frequency is transmitted from the ultrasonic transducer, through interposed soft tissue, and onto the surface of the bone. The carrier wave incident on the bone surface, or other reflection surfaces in the body, is reflected toward the internal surface of the wound. When the carrier wave impinges the internal surface of the wound, at least a portion of the carrier wave is converted into therapeutically beneficial shear waves of acoustic energy, flooding a region of the internal surface of the wound. The shear waves increase vascularization at the internal surface of the wound, thus enhancing growth of epithelial cells. The epithelial cell growth represents healing of the wound. The technique thus promotes healing of the wound from the internal surface of the wound.

The number, position, and size of ultrasonic applicators used at the external skin location are chosen based on the size and position of the wound, and the relative position and proximity of the bone from which the ultrasonic waves are reflected. One or more ultrasonic therapy treatments per day, each having a duration of approximately 20 minutes, is suitable.

BRIEF DESCRIPTION OF THE DRAWINGS

The features of the disclosed therapeutic ultrasound apparatus and method will become more readily apparent and may be better understood by referring to the following detailed description of an illustrative embodiment of the present invention, taken in conjunction with the accompanying drawings, where.

DESCRIPTION OF THE PREFERRED EMBODIMENTS

Figure 1:
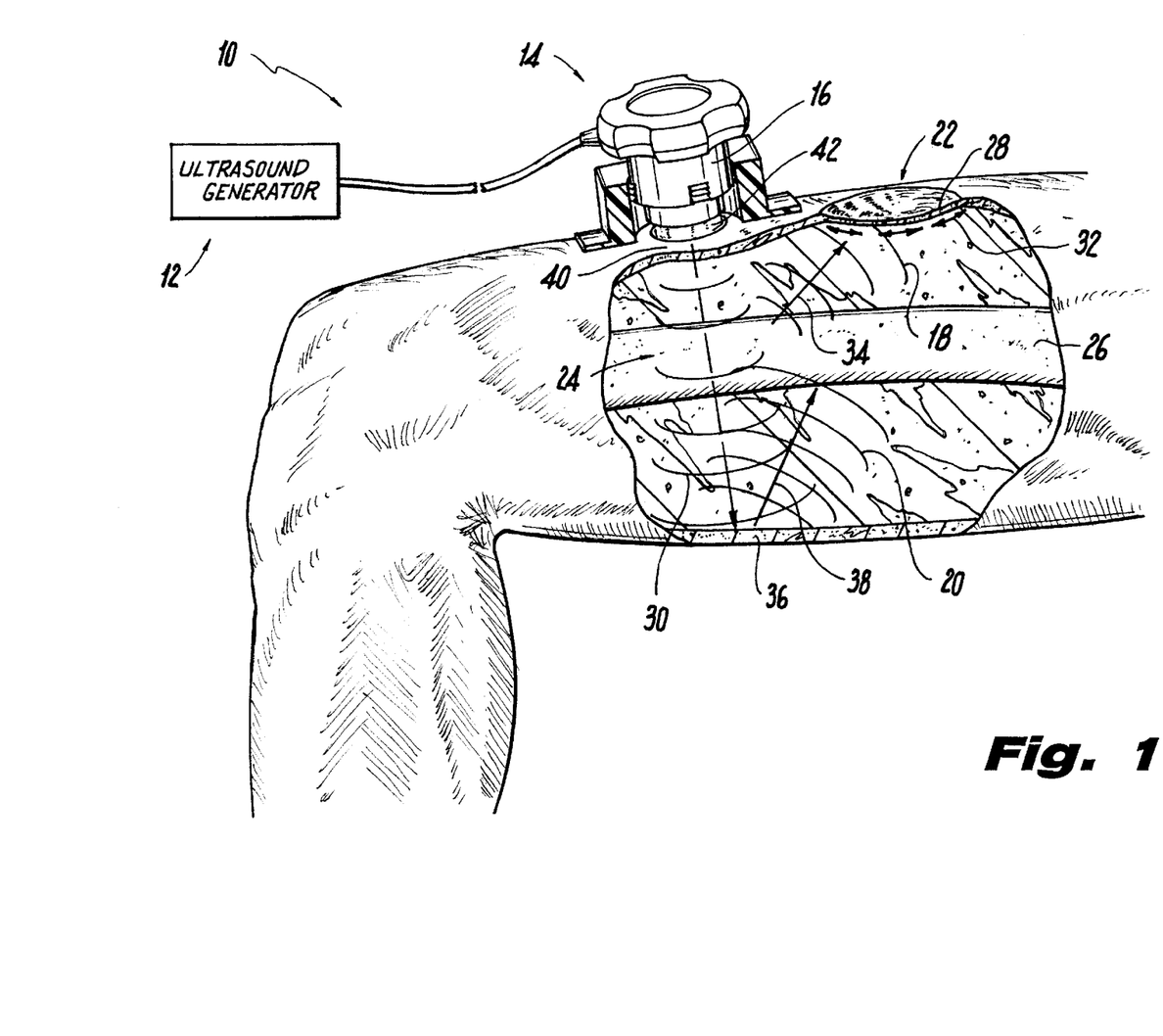
FIG. 1 is a cut-away perspective view showing a device and method of use thereof for wound healing.

Referring now in specific detail to the drawings, with like reference numerals identifying similar or identical elements, as shown in FIG. 1, the present disclosure describes an apparatus 10 and method of use thereof for wound healing, which includes an ultrasonic generator 12 and one or more ultrasonic applicators 14, which include ultrasonic transducers 16 known in the art, for applying ultrasonic waves 18, 20 to a wound 22, such as an ulcer. More than one applicator 14 or transducer 16 may be used to stimulate larger wounds, as needed. The spatial peak temporal average acoustic intensity of the applicators 14 is between about 5 mW/cm$^2$ and about 100 mW/cm$^2$. The carrier frequency and intensity of the ultrasonic treatment is selected by taking into account such factors as: (1) the amount of soft tissue interposed between the external skin location, where the ultrasonic applicator 14 is positioned, (2) the position and cross-section of the bone site 24 from which the ultrasonic waves 18 are reflected, (3) the amount of soft tissue interposed between the bone 26 and the internal surface 28 of the wound 20, and (4) the size, topography and medical characteristics of the internal surface 28 of the wound 20, and, consequently, shear waves or surface acoustic waves (SAW) and longitudinal waves to be generated at the site.

The carrier wave is modulated with an audio signal approximately between 5 Hz and 10 Khz. Low level ultrasound delivers a primary wave called the longitudinal wave 30, which is emitted by the transducer 16 of the applicator 14 as shown in FIG. 1. There are also shear waves or SAW 32 generated by the ultrasound from the transducer 16 which radiate outward along the skin surface. The primary longitudinal wave 30 is partially incident on a bone 26 in the body, and so is partially reflected at a reflection site 24 to generate a reflected portion 34, with the reflected portion 34 directed toward the internal surface 28 of the wound 22. The primary longitudinal wave 30 may also be reflected by other surfaces. For example, as shown in FIG. 1, the internal layer 36 of skin on the opposite side of a limb to the transducer 16 may provide a reflective surface to thus generate additional reflected longitudinal waves 38 directed from the opposite internal skin layer 36 to the wound 22.

When the reflected longitudinal waves 34, 38 impinge on the internal surface 28 of the wound 22, such reflected longitudinal waves 34, 38 are at least partially converted to shear waves or SAW 32 in and around the internal surface 28 of the wound 22, which enhance wound healing at the internal surface 28 by stimulating cell production by the mesenchymal line, thus promoting vascularization and epithelialization.

As shown in the illustrative embodiment in FIG. 1, the ultrasonic applicator 14, including the transducer 16 configured as a modular unit, is placed adjacent an external skin location 40 in the vicinity of the external border of the wound 22. A gel bladder 42, or alternatively a loose conducting gel or other ultrasound conducting media, is positioned between the transducer 16 and the external skin location 40. As shown in FIG. 1, the ultrasound which is transmitted into the soft tissue medium in the form of longitudinal waves 30 diverges as it moves toward the bone 26 or other surfaces such as the skin layer 36 providing reflection. The reflected ultrasound, in the form of longitudinal waves 34, 38, continues to diverge as it approaches the internal surface 28 of the wound 22, so that the ultrasonic treatment delivered to the general site of the wound 22 covers a relatively large region of the internal surface 28 of the wound 22.

Figure 2:
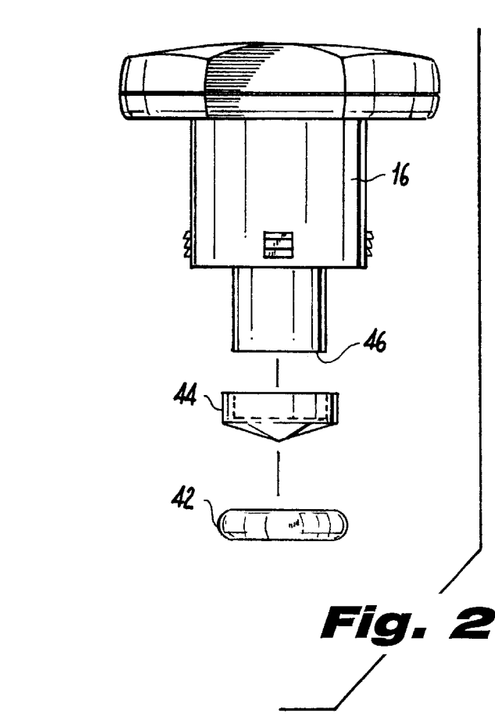
FIG. 2 is a side view of an embodiment of an ultrasound transducer.
Figure 3:
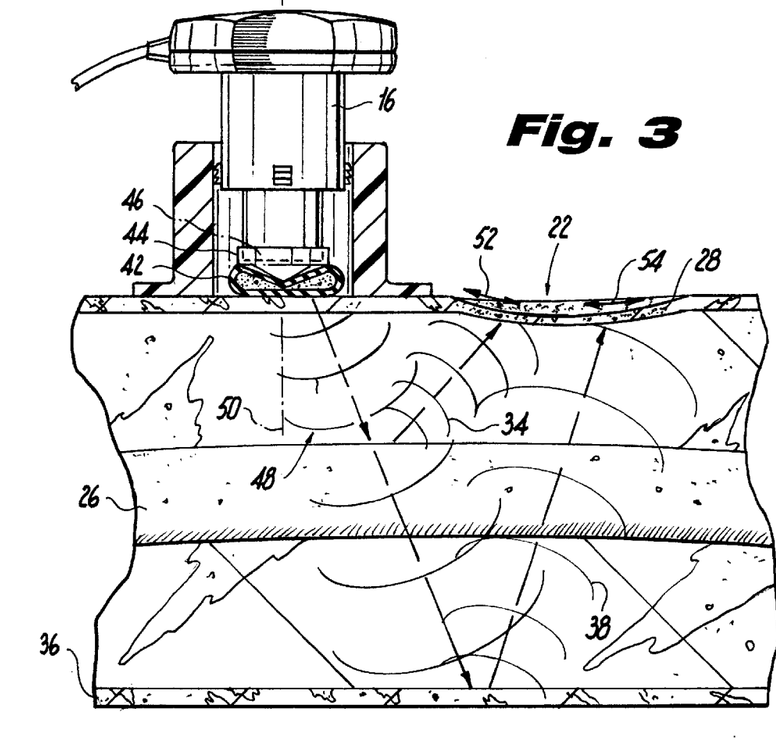
FIG. 3 is a side cross-sectional view of the device using a focusing attachment.

Alternatively, as shown in FIG. 2, the transducer 16 may have an attachment, typically positioned between the operative surface 46 of the transducer 16 and the gel bladder 42, which acts as a focusing element to focus the ultrasound emitted from the operative surface 46 into the soft tissue. In another embodiment, the transducer 16 may be configured to have the focusing element integrally formed with the transducer 16. FIG. 3 shows a side view of the transducer housing of FIG. 2 showing the transducer 16 including the focusing element, illustratively embodied as the attachment 44. Thus, the ultrasound emitted from the transducer 16 in the form of a primary longitudinal wave 30 may be directed at an angle 48 with respect to an axis 50 associated with the transducer and thence toward the bone 26 or other reflective surfaces when the ultrasound enters the soft tissue. The reflected waves 34, 38 also remain relatively focused.

The reflected longitudinal waves 34, 38 may generate respective sets of shear waves or SAW for providing a combined therapeutic treatment to the wound 22. As shown in FIG. 3, the reflected longitudinal wave 34 created by reflection of the primary longitudinal wave 30 off the bone 26 is incident on a portion of the internal surface 28 of the wound 22, thus creating a first set of shear waves 52. The reflected longitudinal wave 38 created by the reflection of the primary longitudinal wave 30 off the opposite side layer 36 of tissue is incident on a separate portion of the wound 22, thus creating a second set of shear waves 54. In addition to this technique, the angle 48 of the ultrasonic emission may be swept and/or modified, either physically or electronically, so that different regions of the internal wound surface 28 may be treated.

In either technique, two or more transducers may be used, as determined by the size, length, etc. of the wound 22. Generally, multiple transducers may be provided at a number of external skin locations around the wound 22 in order to increase the effectiveness of the ultrasonic therapy reflected to the internal surface 28 of the wound 22.

In the illustrative embodiments of FIGS. 1–3, the ultrasonic head module of the ultrasonic applicator 14 includes the transducer 16 of an ultrasonic treatment apparatus. For clarity, the fixture structure which holds the head module adjacent the external skin location 40 is omitted. Also omitted are the electronics and other features which ultimately provide the excitation signals for the transducer 16. These are described in further detail in the above-referenced patents and patent applications, which have been incorporated by reference.

Alternatively, or in conjunction, the at least one ultrasonic applicator 14 may be moved, or may be configured to be movable, to a different external skin location adjacent the wound 22 in order to provide treatment to various portions of the wound 22. Varying the position of the at least one ultrasonic applicator, including moving the transducer 16 circularly or linearly along the skin, also provides treatment of varying intensity at portions of the wound 22.

The transducer 16 itself may also be configured to vibrate with respect to a given external skin location, so that the longitudinal waves 30 generated therefrom and transmitted through the soft tissue are more uniform, thus providing more uniform treatment, including more uniform shear waves, at the internal wound surface 28 where the reflected longitudinal waves 34, 38 impinge. The transducer 16 may be made to vibrate with respect to a housing (not shown in FIGS. 1–3 for clarity) which holds the transducer 16 adjacent an external skin location to accomplish such uniformity of longitudinal waves 30.

The focusing of ultrasonic waves described with respect to FIGS. 2–3 above is illustratively shown with a substantially planar operative surface 46 and a substantially conical attachment 44. In alternative embodiments, the focusing of ultrasonic waves may be provided by configuring the transducer 16 with non-planar surfaces such as non-planar operative surfaces or non-planar segments to generate and emit ultrasound with different propagation characteristics in order to allow differing patterns and intensities of ultrasonic waves to be transmitted toward the internal surface 28 of the wound 22. This provides a variety of therapeutic ultrasonic stimulation and treatment at the internal surface 28.

For example, the transducer segments may be pie shaped, annular rings, or other configurations, which may be activated separately or in unison. Alternatively, or in conjunction, the transducer 16 may be provided with a modal converter or transducer lens, which may also change the pattern of the ultrasound emitted from the transducer 16.

The carrier frequency and/or the modulating frequency may also be varied or swept through a range of frequencies in order to provide a variety of treatments to the internal wound surface 28. The frequencies may be varied either in a continuous manner, or discrete changes may be made in the applied frequency. Varying the carrier and/or modulating frequency is especially useful in applying ultrasonic treatment to promote a variety of stages of cell regeneration in approximately the same region during the same therapy session.

Figure 3A:
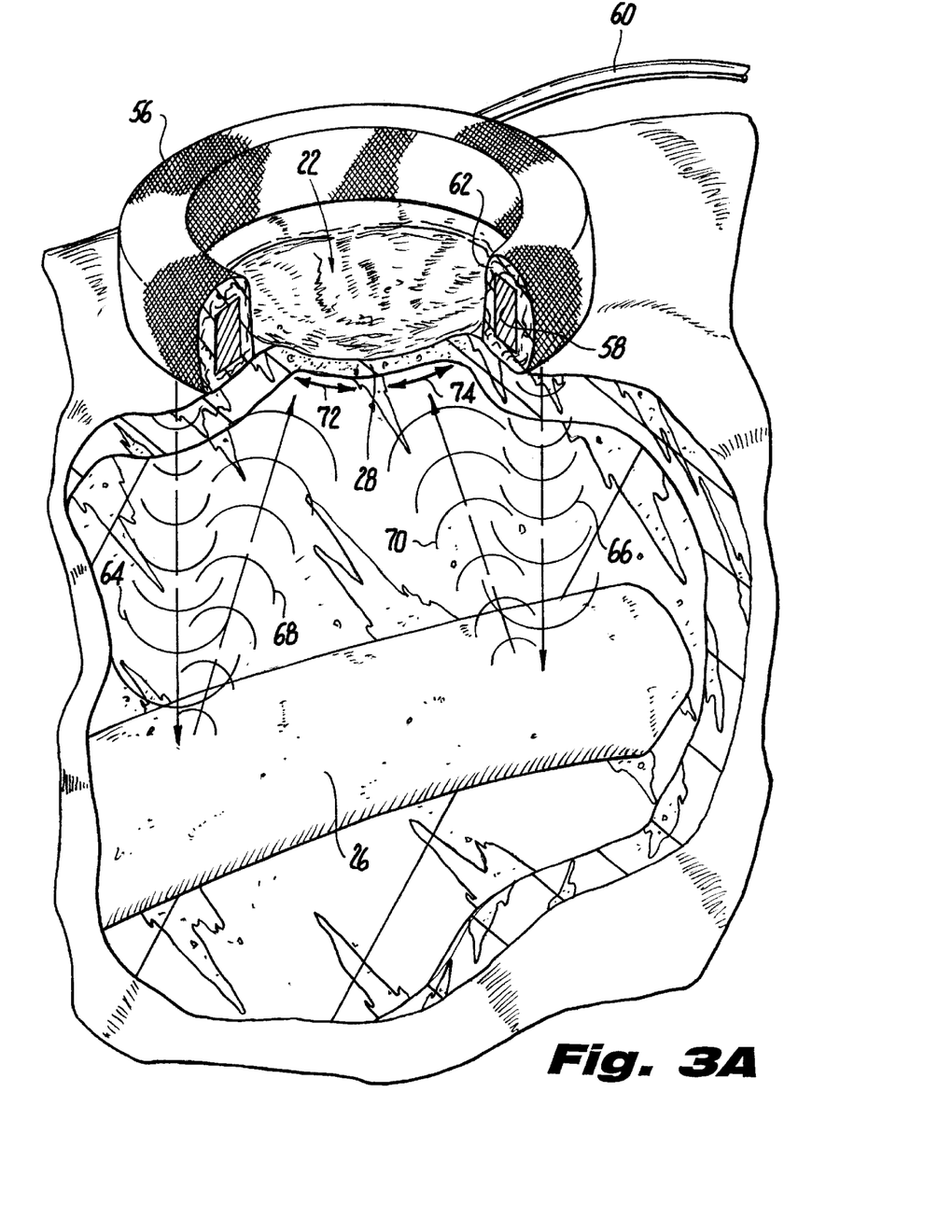
FIG. 3A is a cut-away perspective view of an alternative embodiment of the transducer configured to have an annular shape and a woven fabric covering.

In an alternative embodiment, FIG. 3A illustrates treatment of a wound 22 such as a venous ulcer as in FIGS. 1–3, but utilizing an annular-shaped transducer 56 having a curved operative surface 58 (shown in a cut-away perspective view in FIG. 3A) composed of a composite piezoelectric material attached by a connector 60 to an ultrasonic generator (not 9 shown in FIG. 3A), in which the composite piezoelectric material disposed in a woven fabric 62 or a semi-permeable member provides ultrasonic conductivity between the transducer 56 and the skin of the patient. The woven fabric 60 may have either a hard or a pliable construction, and may be composed of material conductive of ultrasound. Alternatively, the woven fabric 60 may be porous for retaining and releasing ultrasound conductive gel.

The transducer 56 is cut or constructed to surround the external surface of the wound 22. When the appropriate RF signals are applied, the composite piezoelectric material of the transducer 56 emits ultrasonic waves having the therapeutic parameters previously described. Primary longitudinal waves 64, 66 are emitted from the composite piezoelectric material into the body, as shown in FIG. 3A, and reflected from the surface of the bone 26 or from other reflective interfaces, to generate reflected longitudinal waves 68, 70, respectively, which are directed onto the internal surface 28 of the wound 22, thus creating therapeutic shear waves 72, 74, respectively. It is understood that the composite piezoelectric material may completely surround the wound 22; thus, the primary longitudinal waves 64, 66 are emitted from around the entire wound, reflected from the reflecting material, and incident on the internal surface 28 of the wound 22, thereby flooding the internal surface 28 of the wound 22 with the induced shear waves 72, 74.

While the embodiments of the present invention described above refer to the reflection of a primary longitudinal wave from a bone to an internal surface of a wound, the present invention also encompasses delivery of ultrasound to the internal surface of the wound where there is no bone or other reflecting surface in the vicinity of the wound, as described below in further detail with reference to FIGS. 4–11.

Figure 4:
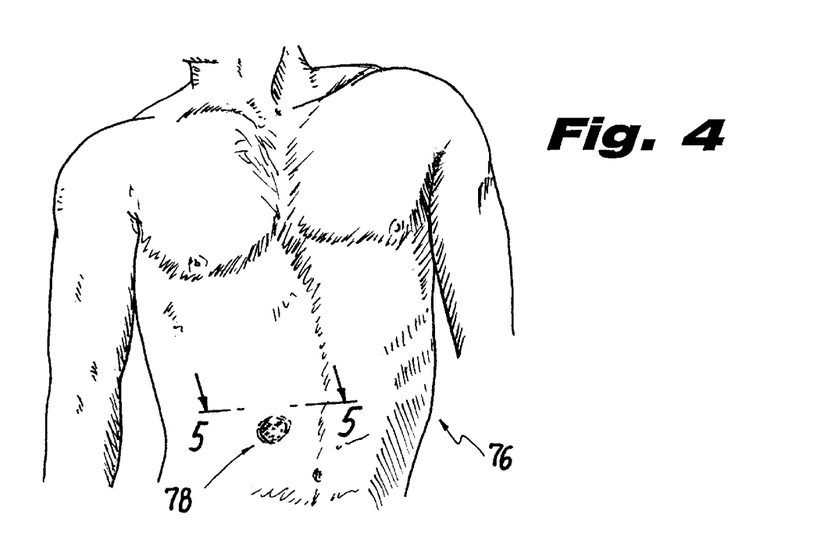
FIG. 4 is a frontal view of a typical wound disposed on a torso.
Figure 5:
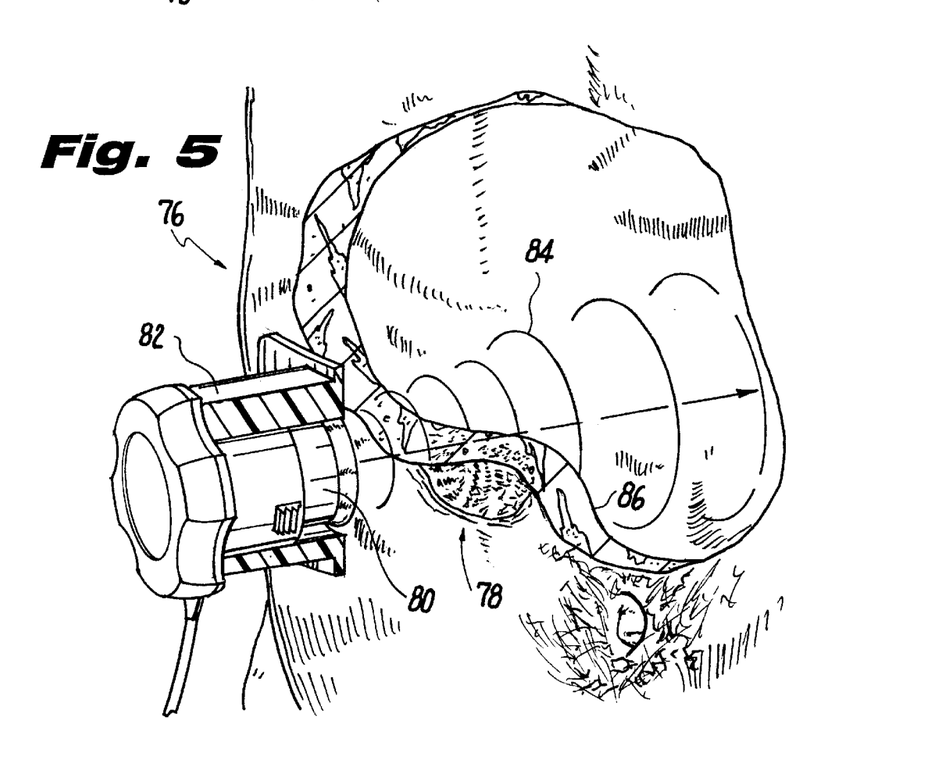
FIG. 5 is a cut-away perspective view of the wound healing device disposed near the wound in the torso.

FIG. 4 illustrates the front of a male torso 76 having a wound 78 on the stomach. The views illustrated in FIGS. 5–11 are cross-sectional views of FIG. 4 taken across lines 5—5. As shown in FIG. 5, a transducer 80 is positioned in a transducer housing 82 disposed upon the external skin of the torso 76 adjacent to the external border of the wound 78, and a longitudinal wave 84 emitted from the transducer 80 penetrates far into the body before it is reflected off a surface internal to the torso 76 such as the spine or any internal organs such as the lungs, stomach, or intestines, which may contain gases such as air, with reflected longitudinal waves then directed onto the internal surface 86 of the wound 78. This is especially true when the person is overweight, or when the cross-section of available reflecting surfaces is small and/or uneven. The longitudinal wave 84 may provide some therapeutic healing of the wound 78, but the intensity of the reflected wave incident on the internal surface 86 of the wound 78 may be too attenuated to provide the necessary therapeutic treatment.

Figure 6:
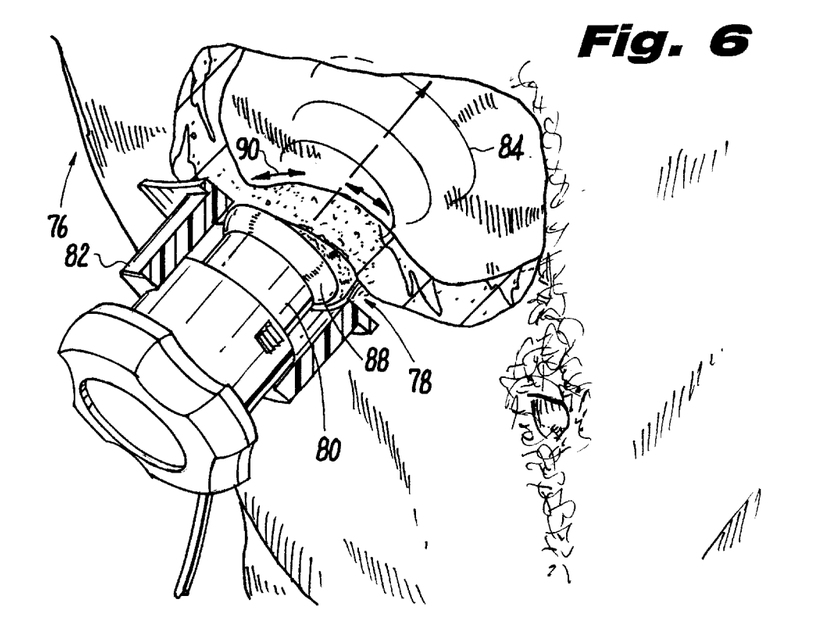
FIG. 6 is a cut-away perspective view of the wound healing device applied to a wound in conjunction with a gel bladder.

FIG. 6 shows an alternative method and embodiment of treating such wounds of the torso 76, in which a gel bladder 88 is interposed between the external surface of the wound 78 and the operative surface of the transducer 80. The longitudinal wave 84 emitted from the transducer 80 travels directly through the gel bladder 88 and into the wound 78, thus creating a shear wave 90 when the longitudinal wave 84 is incident on the internal surface of the wound 78. The gel bladder 88 is to be sterile, especially if the wound 78 is open, and may be impregnated with medication, such as an antibacterial ointment, which flows into the wound 78 and/or its surface during the ultrasonic treatment.

Figure 7:
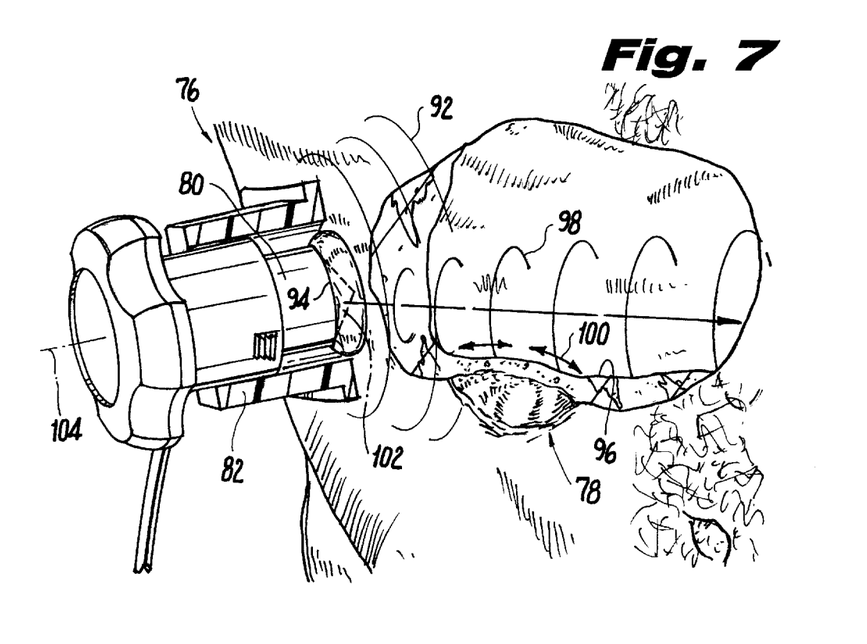
FIG. 7 is a cut-away perspective view of the wound healing device causing an indentation of the torso to orient the transducer for healing the wound.

FIG. 7 illustrates another method and device for treating the wound 78 of a torso 76, in which the transducer 80 is pressed against the external surface of the lower torso, such as approximately adjacent the stomach, to be positioned near the wound 78. By pressing the transducer housing 82 against the external region of the stomach, a local indentation 92 is created. The transducer housing 82 may be turned as it is pressed inward, so that the operative surface 94 of the transducer 80 is directed in the general direction toward the internal surface 96 of the wound 78 within the indentation 92. As shown, the longitudinal wave 98 emitted is incident directly on at least a portion of the internal surface 96 of the wound 78, thus inducing therapeutic shear waves 100. If a specially configured transducer, or alternatively a transducer attachment 102, is used, such as shown in FIG. 3, for focusing the ultrasound in a specific direction, the longitudinal wave 98 may be emitted off of a center axis 104 of the transducer 80, for example, in a direction toward the internal surface 96 of the wound 78, without the need for turning the transducer housing 82 as it is pressed against the skin.

Figure 8:
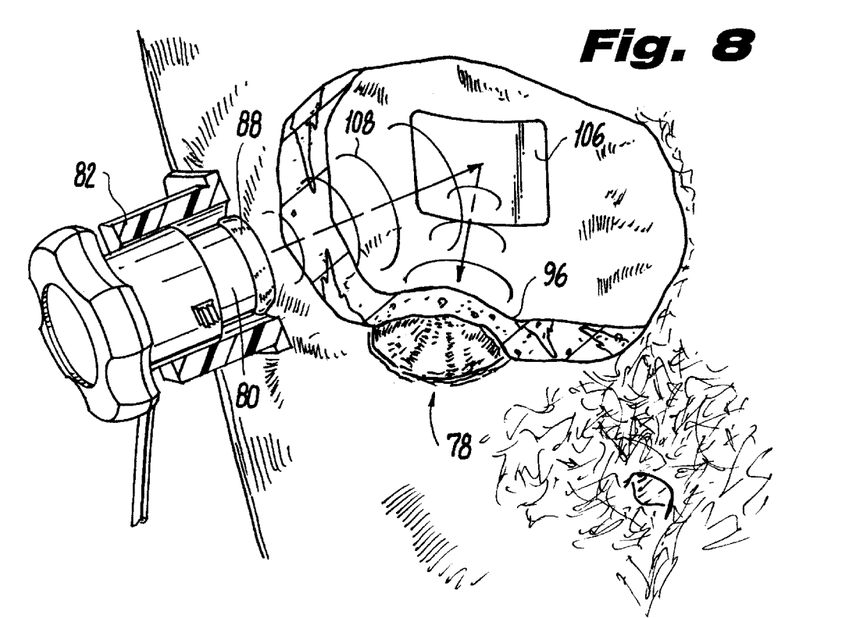
FIG. 8 is a cut-away perspective view of the wound healing device operating in conjunction with an internally disposed reflecting medium.

FIG. 8 illustrates another method and device for treating a wound 78, in which a reflecting medium 106 is inserted into the body in the proximity of the internal surface 96 of the wound 78. The properties of the reflecting medium 106 provide for the reflection of the longitudinal wave 108 toward the internal surface 96 of the wound 96, as if a bone were present, such as described above with reference to FIGS. 1–3A. The reflecting medium 106 may be composed of a variety of materials, and may be fixed in the body or inserted temporarily. For example, the reflecting medium 106 may be a metallic plate, a gas filled pouch, or other quasi-permanent inserts. The reflecting medium 106 may be also be, for example, a contrast agent composed of, for example, bubbles in a gelatin, which is injected intravenously prior to the treatment. In one embodiment, the contrast agent may be absorbable by the body in a relatively short period, thus the contrast agent acts as a temporarily inserted reflecting medium.

Figure 9:
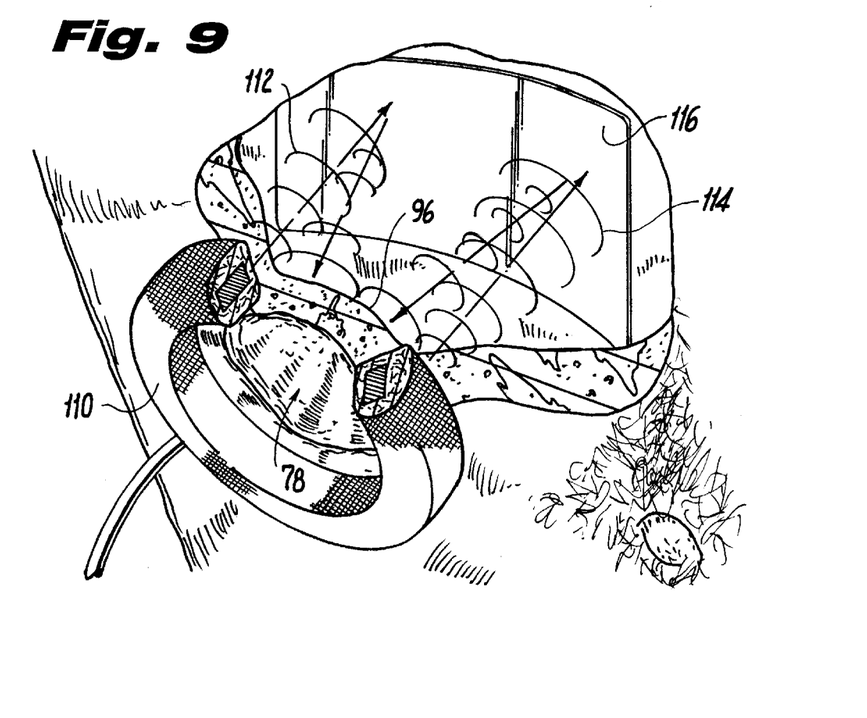
FIG. 9 is a cut-away perspective view of an alternative configuration of the wound healing device having an annular configuration and a woven fabric covering and operating in conjunction with an internally disposed reflecting medium.

An inserted reflecting medium 106, as described with respect to FIG. 8 above, performs particularly well in conjunction with a piezoelectric ultrasonic material or device. As shown in FIG. 9, the piezoelectric ultrasonic device 110 may be embodied as the device 56 described above with respect to FIG. 3A. The piezoelectric ultrasonic device 110 may be configured to surround the exterior boundary of the wound 78. As shown in FIG. 9, illustrative examples of the longitudinal waves 112, 114 generated from the piezoelectric ultrasonic device 110 surrounding the wound 78 are reflected off of an internally disposed medium 116 and onto the internal surface 96 of the wound 78, thereby generating therapeutic shear waves (not shown in FIG. 9) at the internal surface 96 of the wound 78. It is understood that the piezoelectric ultrasonic device 110 completely surrounds the wound 78; thus, longitudinal waves not limited to the illustrative examples of longitudinal waves 112, 114 are emitted around the entire wound 78, reflected from the reflecting material 116, and incident on the internal surface 96 of the wound 78, to flood the internal surface 96 of the wound 78 with induced shear waves.

Figure 10:
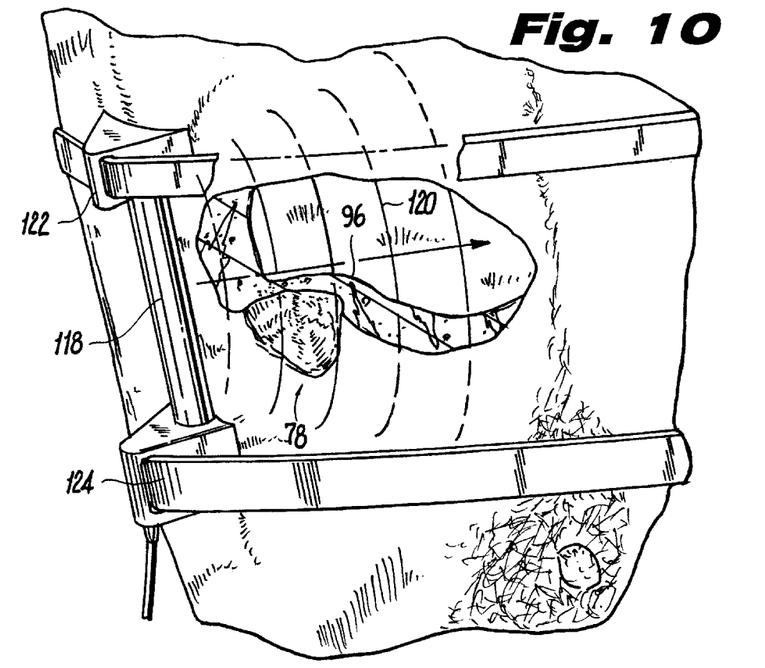
FIG. 10 is a cut-away perspective view of an alternative configuration of the wound healing device having a rod-like configuration.

In an alternative embodiment shown in FIG. 10, an ultrasonic transmitting rod 118 is provided which emits at least one longitudinal wave 120 radially from the axis of the ultrasonic transmitting rod 118. The rod 118 may be composed of, for example, a composite piezoelectric material, and the rod 118 is secured to the patient by a harness apparatus 122, 124 such that the rod 118 is pressed against the skin adjacent the wound 10, and a portion of the longitudinal wave 120 is incident on the internal surface 96 of the wound 78, thus inducing therapeutic shear waves (not shown in FIG. 10).

Figure 11:
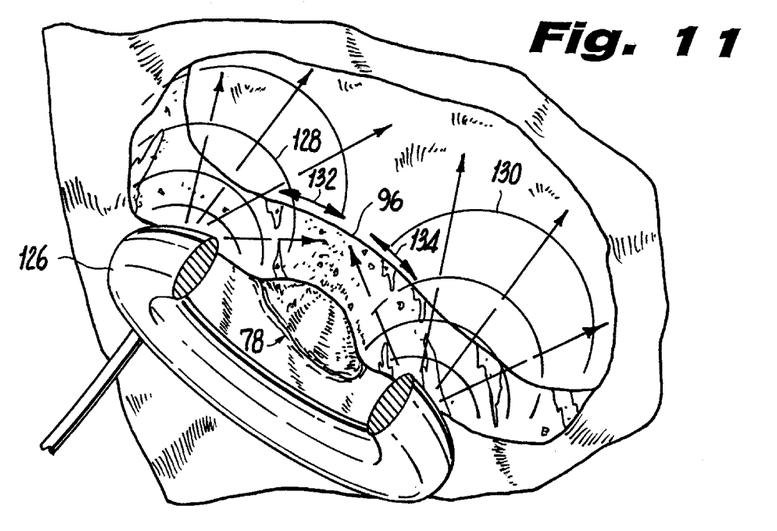
FIG. 11 is a cut-away perspective view of an alternative configuration of the wound healing device having an annular configuration without a woven fabric covering.

In another alternative embodiment shown in FIG. 11, an ultrasonic transmitting ring 126 is provided which emits longitudinal waves 128, 130 radially from the surface of the ring 126. The ring may be composed of, for example, a composite piezoelectric material, and may be configured in a manner similar to the piezoelectric ultrasonic devices 56 and 110 in FIGS. 3A and 9, respectively, without the woven fabric to act as an ultrasonic conductor. Accordingly, ultrasonic conductive gel may be used with the ring 126 of FIG. 11. With the ring pressed against the skin surrounding the wound 78, a portion of the longitudinal waves 128, 130 emitted from the ring 126 is incident on the internal surface 96 of the wound 78, thus inducing therapeutic shear waves 132, 134. It is understood that the ring 126 may be configured to completely surrounds the wound 78; thus, longitudinal waves including the illustrative longitudinal waves 128, 130 are emitted from around the entire wound 78 and incident on the internal surface 96 of the wound 78, to flood the internal surface 96 of the wound 78 with induced shear waves 132, 134.

Figure 12:
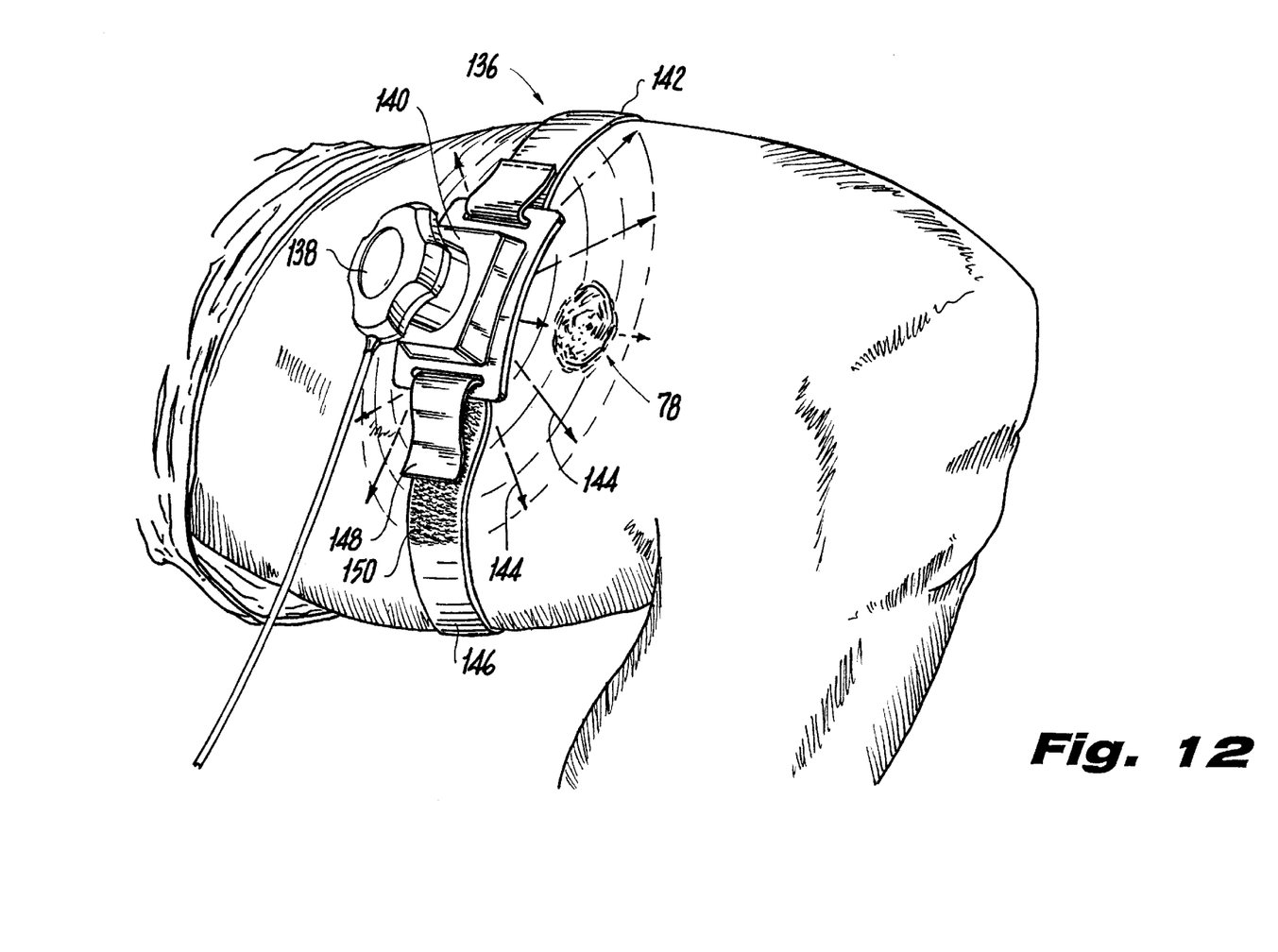
FIG. 12 is a perspective view of an alternative configuration of the wound healing device attachable to a thigh for healing a wound thereupon.

In an alternative configuration shown in FIG. 12, the wound healing device 136 includes a transducer 138 positioned in a housing 140 which is secured by an adjustable securing structure 142 to a thigh for healing a wound 78 thereupon, with the transducer 138 emitting longitudinal ultrasonic waves 144 which generate shear waves (not shown in FIG. 12) upon contact with the internal surface of the wound 78. In an illustrative embodiment, the adjustable securing structure 142 shown in FIG. 12 includes an adjustable strap 146 having a first portion 148 engaging a second portion 150 using hook and link fasteners. Alternatively, a belt with a buckle and notches may be used, or a sterile adhesive strip for adhering to the thigh.

As noted above, the term "wound" as used herein, has a broad meaning, generally encompassing addressing damage to, repair of, or restoration of soft tissue. The present invention may be used, for example, to prevent surgical adhesions, by stimulating the proper repair of surgical incisions. It may also prevent or arrest wound dehiscence, by promoting vascularization at the surfaces adjacent surgical incisions. It may also be used in cosmetic surgery, for example, by enhancing the healing of hair transplants, or by directly stimulating regeneration of cells.

Accordingly, modifications such as those suggested above, but not limited thereto, are to be considered within the scope of the invention.

What is claimed is:

1. A portable therapeutic device for healing a wound comprising:
    an ultrasonic transducer having:
    a rod-shaped operative surface having an axis for emitting ultrasound radially toward the wound for the healing thereof; and
    means for fastening the ultrasonic transducer to an exterior portion of a patient's body to secure the operative surface substantially adjacent to the wound and simultaneously applying a force to the ultrasonic transducer against the skin adjacent the wound to direct the operative surface of the ultrasonic transducer in a direction toward the wound.

2. The portable therapeutic device of claim 1, wherein the rod-shaped operative surface is configured to propagate the ultrasound as at least as one longitudinal wave to generate shear waves therefrom at an internal surface of the wound for the healing thereof.

3. The portable therapeutic device of claim 2, wherein the rod-shaped operative surface is configured to propagate the at least one longitudinal wave radially from the axis of the rod-shaped operative surface.

4. The portable therapeutic device of claim 1, wherein the rod-shaped operative surface includes a composite piezoelectric material.

5. The portable therapeutic device of claim 1, wherein the means for fastening includes at least two harness straps which are strapped to the exterior portion of the patient's body for securing the rod-shaped operative surface of the ultrasonic transducer in proximity to the wound and for applying a force to the ultrasonic transducer to direct the rod-shaped operative surface of the ultrasonic transducer in the direction toward the wound.

6. A method for healing a wound comprising:
    positioning an ultrasonic transducer having a rod-shaped operative surface substantially adjacent to the wound;
    fastening the ultrasonic transducer to an exterior portion of a patient's body to secure the operative surface, substantially adjacent to the wound;
    applying a force during the fastening step to the ultrasonic transducer against the skin adjacent the wound to direct the operative surface of the ultrasonic transducer in a direction toward the wound;
    emitting ultrasound from the operative surface toward the wound and away from the wound to contract the wound for causing the healing thereof; and
    reflecting the ultrasound emitted away from the wound toward the direction of the wound for causing the healing thereof.

7. A portable therapeutic device for healing a wound comprising;
    an ultrasonic transducer having:
    a rod-shaped operative surface having an axis for emitting ultrasound radially toward the wound for the healing thereof; and
    a fastener for securing the ultrasonic transducer to an exterior portion of a patient's body where the operative surface is brought substantially adjacent to the wound and for simultaneously applying a force to the ultrasonic transducer against the skin adjacent the wound to direct the operative surface of the ultrasonic transducer in a direction toward the wound.

8. The portable therapeutic device of claim 7, wherein the rod-shaped operative surface propagates the ultrasound as at least as one longitudinal wave to generate shear waves therefrom at an internal surface of the wound for the healing thereof.

9. The portable therapeutic device of claim 8, wherein the at least one longitudinal wave propagates radially from the axis of the rod-shaped operative surface.

10. The portable therapeutic device of 7, wherein the rod-shaped operative surface includes a composite piezoelectric material.

11. The portable therapeutic device of claim 7, wherein the rod-shaped operative surface is secured to an area adjacent to the wound of a patient by a harness apparatus.

* * * * *